United States Patent
Flexman et al.

(10) Patent No.: US 11,551,380 B2
(45) Date of Patent: Jan. 10, 2023

(54) AUGMENTED REALITY INTERVENTIONAL SYSTEM PROVIDING CONTEXTUAL OVERLAYS

(71) Applicant: KONINKLIJKE PHILIPS N.V., Eindhoven (NL)

(72) Inventors: Molly Lara Flexman, Melrose, MA (US); Aleksandra Popovic, Boston, MA (US); Ashish Panse, Burlington, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 739 days.

(21) Appl. No.: 16/478,135

(22) PCT Filed: Jan. 15, 2018

(86) PCT No.: PCT/EP2018/050806
§ 371 (c)(1),
(2) Date: Jul. 16, 2019

(87) PCT Pub. No.: WO2018/134140
PCT Pub. Date: Jul. 26, 2018

(65) Prior Publication Data
US 2019/0371012 A1   Dec. 5, 2019

Related U.S. Application Data

(60) Provisional application No. 62/447,069, filed on Jan. 17, 2017.

(51) Int. Cl.
*G06T 11/00* (2006.01)
*A61B 34/00* (2016.01)
(Continued)

(52) U.S. Cl.
CPC .............. *G06T 11/00* (2013.01); *A61B 34/25* (2016.02); *A61B 90/37* (2016.02); *G09B 5/02* (2013.01);
(Continued)

(58) Field of Classification Search
None
See application file for complete search history.

(56) References Cited

U.S. PATENT DOCUMENTS 10,706,626 B1 * 7/2020 Brent .................. G06V 10/462
2014/0275760 A1   9/2014 Lee et al.
(Continued)

FOREIGN PATENT DOCUMENTS

| EP | 2982415 A1 | 2/2016 |
| WO | 2014013393 A2 | 1/2014 |
| WO | 2016195401 A1 | 12/2016 |

OTHER PUBLICATIONS

Talbot et al. "A method for patient set-up guidance in radiotherapy using augmented reality", Australasian Physical & Engineering Sciences in Medicine vol. 32 No. 4, 2009 (Year: 2009).*

(Continued)

*Primary Examiner* — Yingchun He

(57) ABSTRACT

An augmented reality interventional system which provides contextual overlays (116) to assist or guide a user (101) or enhance the performance of the interventional procedure by the user that uses an interactive medical device (102) to perform the interventional procedure. The system includes a graphic processing module (110) that is configured to generate at least one contextual overlay on an augmented reality display device system (106). The contextual overlays may identify a component (104) or control of the interactive medical device. The contextual overlays may also identify steps of a procedure to be performed by the user and provide instructions for performance of the procedure. The contex- (Continued)

tual overlays may also identify a specific region of the environment to assist or guide the user or enhance the performance of the interventional procedure by identifying paths or protocols to reduce radiation exposure.

14 Claims, 6 Drawing Sheets

(51) Int. Cl.
  *A61B 90/00* (2016.01)
  *G16H 30/20* (2018.01)
  *G16H 40/63* (2018.01)
  *G09B 5/02* (2006.01)
  *G09B 19/00* (2006.01)

(52) U.S. Cl.
  CPC ........... *G09B 19/003* (2013.01); *G16H 30/20* (2018.01); *G16H 40/63* (2018.01); *A61B 2034/252* (2016.02); *A61B 2090/365* (2016.02); *A61B 2090/3764* (2016.02); *G06T 2200/24* (2013.01); *G06T 2210/41* (2013.01)

(56) References Cited

U.S. PATENT DOCUMENTS

2015/0201892 A1* 7/2015 Hummel ............... G06T 19/006
 348/77
2015/0281680 A1* 10/2015 Grafenberg .......... H04N 13/221
 348/50
2016/0191887 A1 6/2016 Casas

OTHER PUBLICATIONS

PCT/EP2018/050806, ISR and Written Opinion, dated Apr. 20, 2018, 18 Page Document.
Flexman et al: "Augmented Reality for Radiation Dose Awareness in the Catheterization Lab"; Siggraph 2017, 2 Page Article.

* cited by examiner

AUGMENTED REALITY INTERVENTIONAL SYSTEM PROVIDING CONTEXTUAL OVERLAYS

CROSS-REFERENCE TO PRIOR APPLICATIONS

This application is the U.S. National Phase application under 35 U.S.C. § 371 of International Application No. PCT/EP2018/050806, filed on Jan. 15, 2018, which claims the benefit of U.S. Provisional Patent Application No. 62/447,069 filed on Jan. 17, 2017. These applications are hereby incorporated by reference herein.

BACKGROUND

Technical Field

This disclosure relates to augmented reality systems and methods, and more particularly to systems and methods for performing augmented reality interventional procedures featuring contextual overlays.

Description of the Related Art

A hybrid operating room (OR) and catheter laboratory (cathlab) support a broad range of imaging protocols. The number and type of these protocols can be complicated to optimally find a correct protocol for each step of a procedure. In addition, challenges arise when attempting to introduce new protocols, features, and tools without assistance during a procedure.

In one example, interventional x-ray suites provide a huge range of features and tools to optimize imaging, acquire various image formats, and perform complex protocols. User interaction is typically performed via modules such as an imaging module, geometry module, xper module, and review module as well as through typical on-screen interactions via keyboard, mouse, and monitors (such as, data and review monitors).

Augmented reality generally refers to a situation when a live image stream is supplemented with additional computer-generated information. The live image stream can be provided using the eye, cameras, smart phones, tablets, etc. This image stream is augmented by a display to the user. The augmented display can be conveyed to the user via glasses, contact lenses, projections or on a live image stream device (e.g., smart phone, tablet, etc.).

It would be advantageous to provide an augmented reality interventional system which includes contextual overlays to provide assistance or guidance to the user or to enhance the user's performance of an interventional procedure.

SUMMARY

In accordance with the present principles, a medical interventional system is provided. The medical interventional system includes an interactive medical device which includes a plurality of components. An augmented reality display device is configured for being viewed by a user during the performance of an interventional procedure in an environment using the interactive medical device. A graphic processing module is configured to generate a contextual overlay on the augmented reality display device to assist or enhance the user's performance of the interventional procedure using the interactive medical device.

In another embodiment, a medical interventional system is provided. The medical interventional system includes a workstation that includes one or more processors, memory and an interface. The medical interventional system also includes an interactive medical device which includes a plurality of components. An augmented reality display device is configured for being viewed by a user during the performance of an interventional procedure in an environment using the interactive medical device. A graphic processing module is configured to generate a contextual overlay on the augmented reality display device to assist the user or enhance the user's performance of the interventional procedure using the interactive medical device.

In another embodiment, a method for assisting or enhancing a user's performance of an interventional procedure in an environment using an interactive medical device is provided. The method includes the step of determining a contextual overlay to be generated on an augmented reality display device. The method also includes the step of generating the contextual overlay on the augmented reality display device to assist the user or enhance the user's performance of the interventional procedure.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
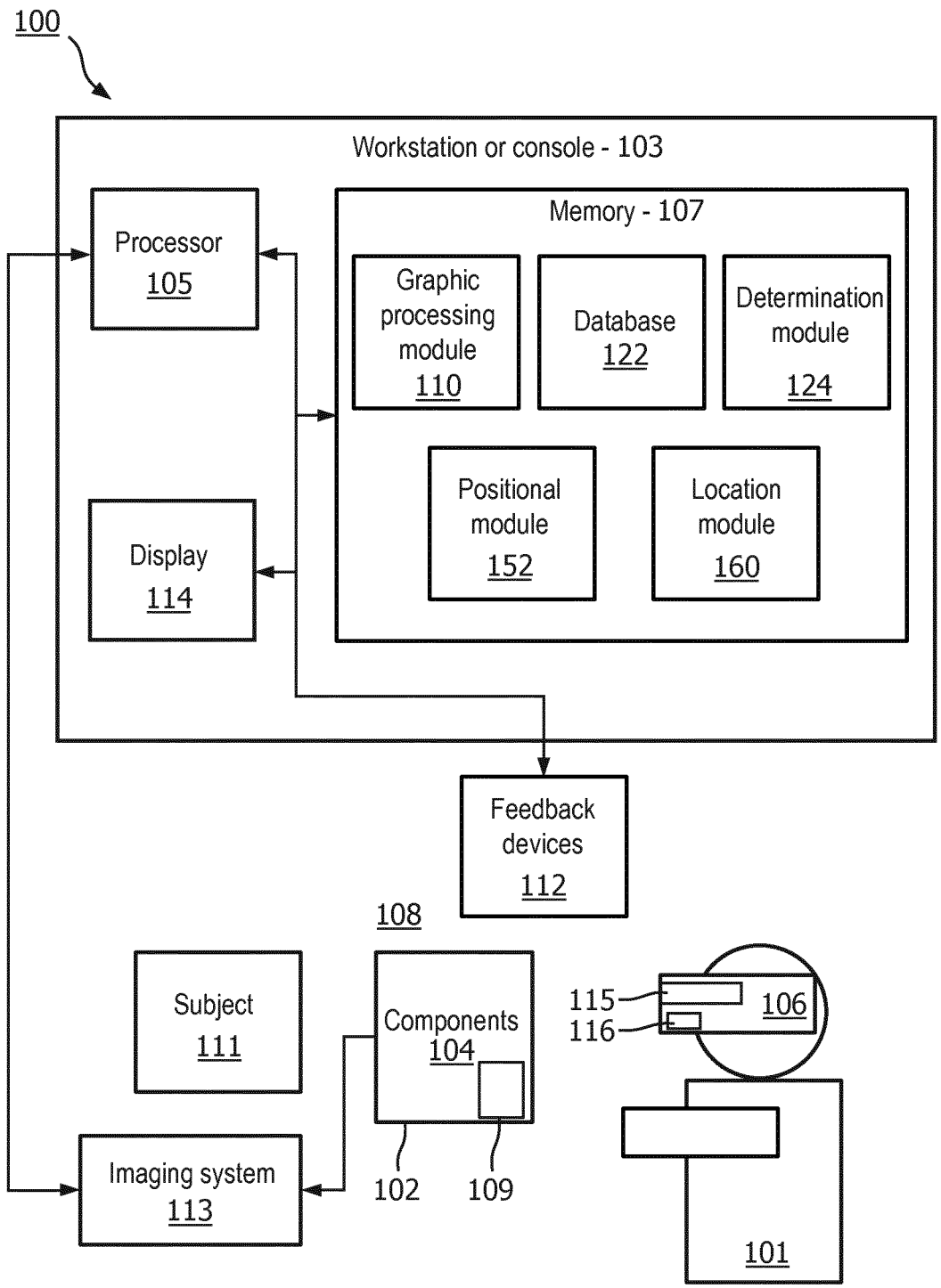
FIG. 1 is a block/flow diagram showing an augmented reality interventional system providing contextual overlays in accordance with one embodiment.

In accordance with the present principles, a system for performing an interventional procedure using augmented reality to provide contextual overlays which assist or guide the user or enhance the performance of the interventional procedure is provided. The system includes an augmented reality display device, such as a head-mounted virtual reality system, which is configured for being viewed by a user during the performance of the interventional procedure using an interactive medical device. A graphic processing module is configured to generate a contextual overlay on the augmented reality display device to assist or guide the user or otherwise enhance the performance of the interventional procedure.

The graphic processing module is configured to generate contextual overlays which may identify a component or control of the interactive medical device and provide instructions to the user concerning the use of the component or control. The contextual overlays may also identify steps of a procedure to be performed by the user and provide instructions for performance of the procedure. The contextual overlays may also identify a specific region of the environment where the interventional procedure is performed.

The graphic processing module may receive input from the user to provide customized contextual overlays. The graphic processing module may also receive feedback and a history of inputted commands in the system to dynamically determine steps of a procedure or to identify particular objects or regions of interest in the environment. The system provides improved clarity with respect to the workflow of an interventional procedure and implementation of the procedure on an interactive medical device. The system improves the efficiency and accuracy of the performance of an interventional procedure. The system also identifies and guides the user with respect to new devices or procedures on the interactive medical device.

It should be understood that the present invention will be described in terms of medical interventional systems; however, the teachings of the present invention are much broader and are applicable to any interventional system. In some embodiments, the present principles are employed in performing interventional procedures for complex biological or mechanical systems. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

It will also be understood that when an element such as a layer, region or material is referred to as being "on" or "over" another element, it can be directly on the other element or intervening elements may also be present. In contrast, when an element is referred to as being "directly on" or "directly over" another element, there are no intervening elements present. It will also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

Referring now to the drawings in which like numerals represent the same or similar elements and initially to FIG. 1, a system 100 for performing an interventional procedure, is illustratively shown in accordance with one embodiment. The system 100 includes an interactive medical device 102. For example, in one embodiment, the interactive medical device is an interventional imaging device such as the Philips ALLURA™ X-ray system. The interactive medical device may include an imaging system 113 configured for reconstruction of the anatomy of the subject 111. The imaging system 113 may be an x-ray system, ultrasound system, IVUS system, navigation system, computed tomography system, magnetic resonance or other imaging systems known in the art.

The interactive medical device 102 includes a plurality of components 104 which may be utilized by the user in performing the interventional procedure. For example, in one embodiment, the components 104 may include modules which are configured to perform specialized functions for the system, such as an imaging module for imaging the subject 111, geometry module for positioning motorized components of the system, a data monitoring module for monitoring data acquired by the system, etc. The components 104 may also include interface devices 109 for user input, such as a keyboard, mouse, a joystick, a haptic device.

The interactive medical device 102 may include a workstation or console 103 from which a procedure is supervised and/or managed. Workstation 103 preferably includes one or more processors 105 and memory 107 for storing programs and applications. Display 114 may also permit a user 101 to interact with the workstation 103 and its components and functions, or any other element within the system 100. This is further facilitated by the interface devices 109 which permit user feedback from and interaction with the workstation 103.

In a preferred embodiment, the system 100 also includes a plurality of feedback devices 112 that are configured to obtain feedback concerning the user 101, the environment 108 and/or the interactive medical device 102 and components 104. The feedback devices 112 may be one or more cameras 115 which provide a camera feed of a user view and/or other view within the environment, eye tracking and/or head tracking of the user. The feedback devices 112 may also be a microphone for obtaining audio from the user 101 or various objects, persons or devices in the environment 108. The feedback devices 112 may also be sensors for determining the position of a portion of the user's body, the device 102 and/or the components 104. For example, a sensor may be placed on an arm or hand of the user to track its motion. The feedback devices 112 may also be one or more motion tracking devices such as accelerometers, infrared tracking, optical fiber tracking, electromagnetic (EM) tracking or other tracking mechanism(s).

The system 100 also includes an augmented reality display device 106 that is configured for being viewed by a user during the performance of an interventional procedure in an environment 108, such as an operating room. For example, in one embodiment, the augmented reality display device 106 may be a head-mounted virtual reality system such as GOOGLE GLASS™, HOLOLENS™, MAGIC LEAP™, VUSIX™. However, the augmented reality display device 106 may be any other virtual reality/augmented reality system known in the art. The augmented reality display device 106 may have a two or three-dimensional capability.

The system further includes a graphic processing module 110 which is configured to generate a contextual overlay 116 on the augmented reality display device 106 on a specific region of the display device corresponding to the user's field of view. The contextual overlay 116 is configured to provide information to the user specifically arranged with respect to the user's field of view to assist or guide the user or enhance the user's performance of the interventional procedure. In some embodiments, the graphic processing module 110 may be configured to receive feedback from the feedback devices 112 in order to determine the specific overlay to generate on the augmented reality display device. The augmented reality display device 106 may be connected to the system through a cable or may be wirelessly connected to the system.

Figure 2:
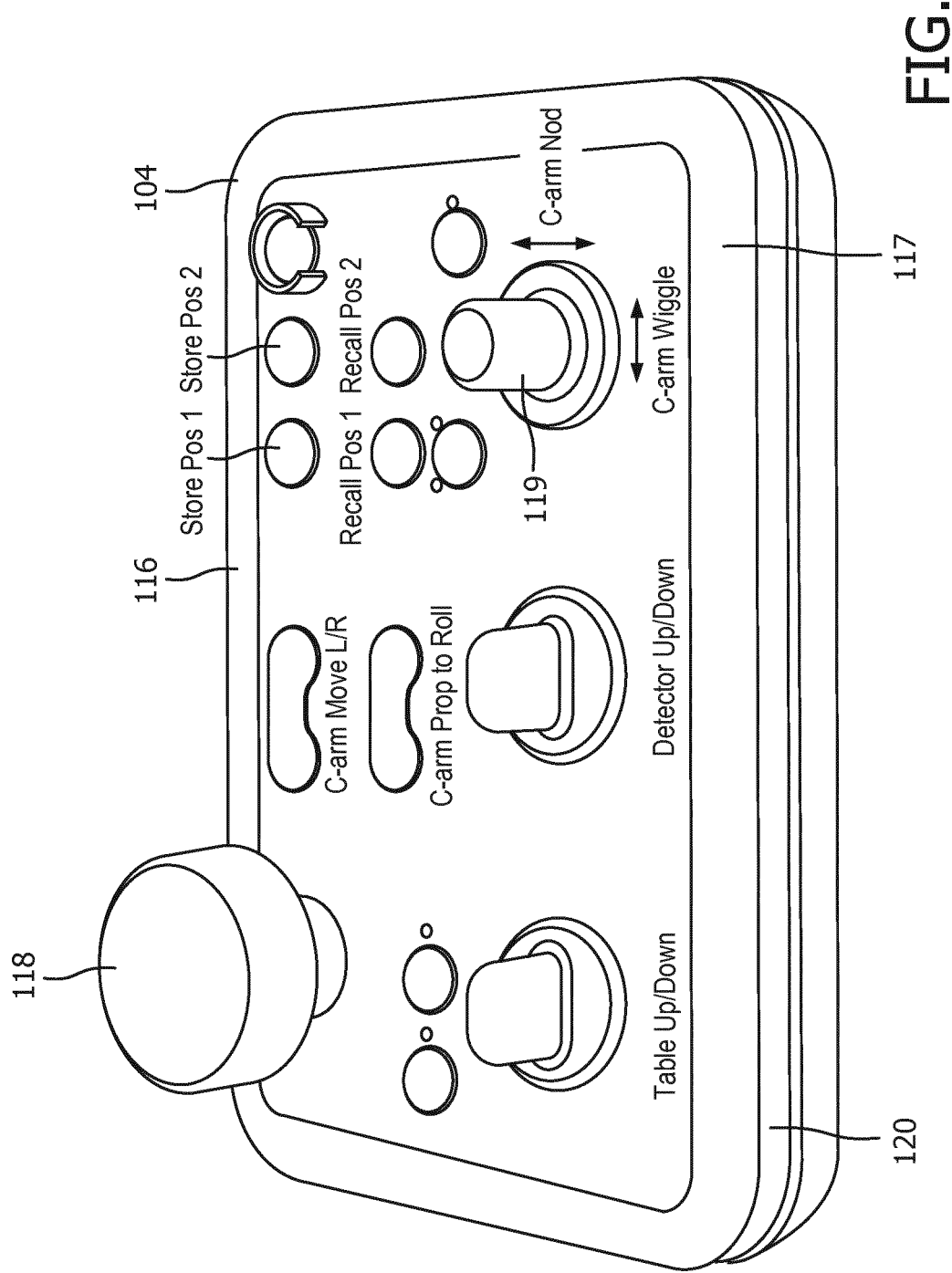
FIG. 2 shows images of contextual overlays displayed on an augmented reality display device in relation to a module.

As shown in FIG. 2, in one embodiment, the graphic processing module 110 is configured to generate contextual overlays 116 for various controls 118 on a component 104 of the interactive medical device. As an example, image 120 in FIG. 2 shows a module 117 of the interactive medical device 102 which includes contextual overlays 116 generated on the augmented reality display device 106 over each control 118 which identify the control and the movement of the control. For example, as shown in FIG. 2, a knob 119 which controls the position of the c-arm may include the user-defined contextual overlay "C-arm Wiggle". The graphic processing module 110 may be configured to generate a contextual overlay 116 for any other component 104 of the interactive system including other modules or devices.

The graphic processing module 110 may receive the information for the contextual overlay from a database 122 stored in the memory 107. In a preferred embodiment, the graphic processing module 110 may also be configured to receive input from the user 101 via the interface 109 concerning the information to be displayed in the contextual overlay 116. This allows the user to customize the contextual overlay based on the user's preferences and/or the specific procedure being performed. The contextual overlays 116 identify and provide information for components and controls of the interactive device 102 that are clearer, more comprehensive and more customizable than existing products, such as physical stickers that are placed on various components or controls.

The graphic processing module 110 may also be configured to generate contextual overlays 116 which guide the user through various steps of a procedure. In one embodiment, the steps of a procedure are stored in the database 122 and the graphic processing module 110 receives information for the appropriate contextual overlays 116 from the database 122. The graphic processing module 110 may also be configured to receive input from the user via the interface 109 in order to customize the contextual overlays 116.

In certain embodiments, the system 100 may include a determination module 124 that is configured to receive information concerning the steps of a procedure being performed from the database 122 and feedback from the feedback devices 112 or a history of signals from components of the system, such as a module, in order to determine the appropriate step(s) for the user to perform. The determination module 124 is then configured to send information to the graphic processing module 110 concerning the contextual overlays 116.

For example, the performance of a 3D reconstruction of target anatomy on an interactive interventional x-ray product is often complex and involves procedures which require numerous steps to be performed accurately and in a specific order. The numerous modules, controls, screens and input devices may be confusing to a user resulting in errors and decreased efficiency in the performance of the interventional procedure.

In order to generate a 3D reconstruction of a target anatomy, the target anatomy may first be isocentered so that the c-arm of the imaging device takes a path that rotates around the target anatomy in a manner wherein the target anatomy of the subject 111 remains in the center of the image. In order to isocenter the target anatomy, the user typically must move a table up or down with the c-arm in a lateral position until the anatomy is centered. The user may then move the table left or right and forward/back with the c-arm in the AP position until the target anatomy is centered. This procedure may be time consuming and requires movement of the table under fluoroscopic guidance.

After the target anatomy is isocentered, the user may perform an image acquisition protocol wherein the end and start positions of the c-arm motion are tested to ensure that the c-arm can freely move through the rotational motion without hitting any objects and that the arm may reach the end and start positions. However, problems in the performance of this procedure frequently occur due to the isocentering not being correctly determined, the user not pressing the correct buttons to move the device through the end and start positions or the c-arm having obstructions in its path. The generation of contextual overlays 116 on the augmented reality display device 106 provides sufficient information to the user to reduce or avoid these problems and to increase the efficiency of the interventional procedure.

Figure 3:
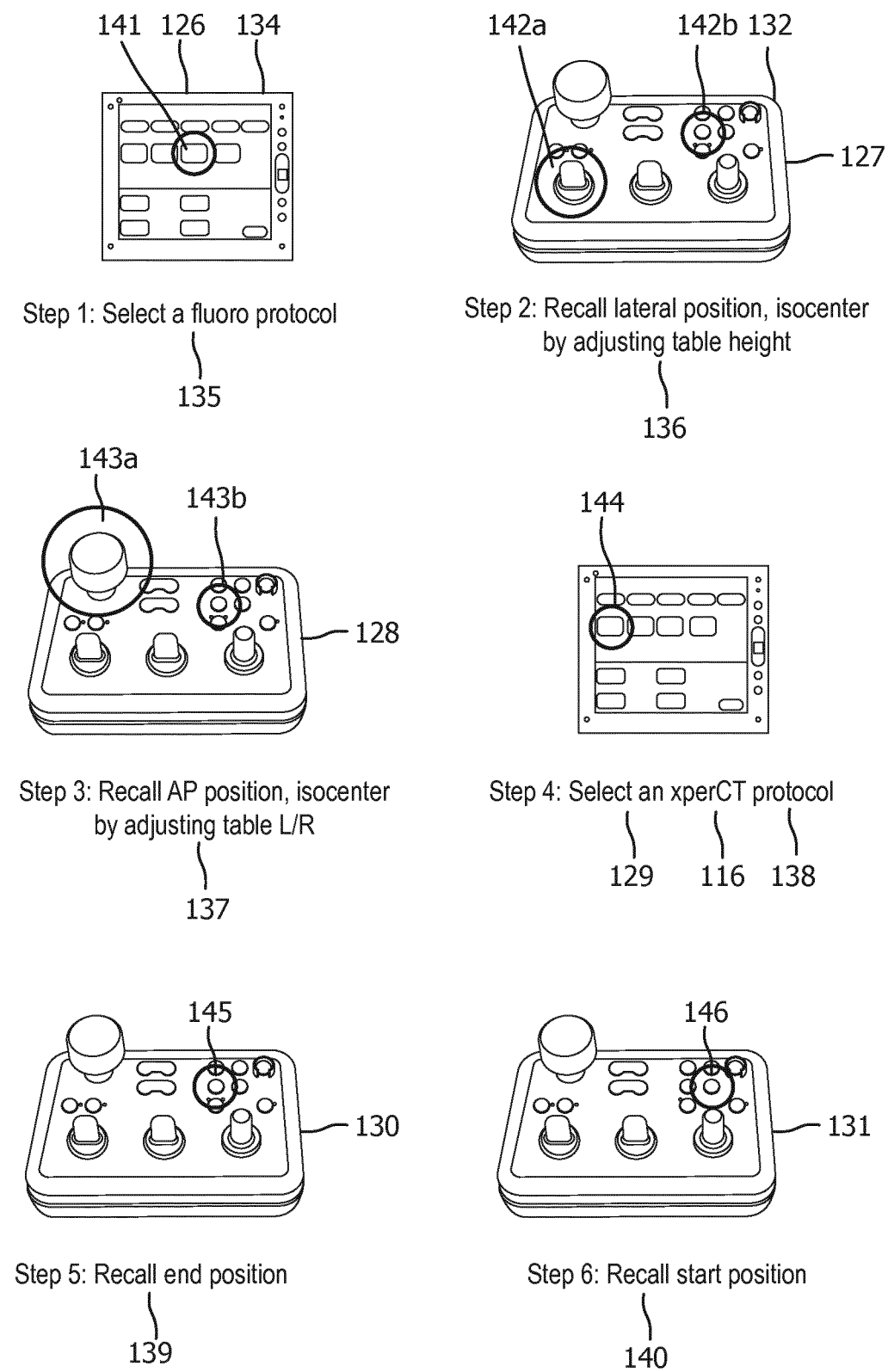
FIG. 3 shows images of contextual overlays which guide the user through steps of a procedure that are displayed on an augmented reality display device in relation to a module and an interactive display device.

For example, as shown in FIG. 3, images 126-131 show contextual overlays 116 displayed on an augmented reality display device 106 in relation to a geometry module 132 and an interactive display device 134 for performing the image acquisition process after isocentering has been performed. The contextual overlays 116 that are generated by the graphic processing module 110 include an identification concerning the order of each step, instructions to perform the step and/or the specific control of the module or region of the interactive display device for the user to perform the actions thereon.

As an example, image 126 shows a contextual overlay 135 that is generated below an interactive display device 134 which states "Step 1: Select a fluoro Protocol". A contextual overlay 141 comprising a circle is generated over the specific region of the interactive display device 134 that the user needs to press or otherwise manipulate in order to select a fluoro protocol.

Image 127 shows a contextual overlay 136 that is generated below a module 132 which states "Step 2: Recall Lateral position, isocenter by adjusting table height". The specific button and knob for recalling the lateral position and adjusting the table height are circled 142a, 142b on the augmented reality display device 106 over these controls.

Image 128 shows a contextual overlay 137 that is generated below a module 132 which states "Step 3: Recall AP position, isocenter by adjusting table L/R". Image 128 also shows contextual overlays 143a, 143b comprising circles that are positioned on the augmented reality display device 106 around the controls which must be manipulated by the user in order to perform these specific steps.

Image 129 shows a contextual overlay 138 that is generated below an interactive display device 134 which states "Step 4: Select an xperCT Protocol". A contextual overlay 144 comprising a circle is generated over the specific region of the interactive display device 134 that the user needs to press or otherwise manipulate to select an xperCT protocol.

Image 130 shows a contextual overlay 139 that is generated below a module 132 which states "Step 5: Recall end position". Image 130 also shows a contextual overlay 145 comprising a circle that is positioned on the augmented reality display device 106 around the button which must be pressed by the user in order to perform this specific step.

Image 131 shows a contextual overlay 140 that is generated below a module 132 which states "Step 6: Recall start position". Image 131 also shows a contextual overlay 146 comprising a circle that is positioned on the augmented reality display device 106 around the button which must be pressed by the user in order to perform this specific step. While these specific embodiments show a contextual overlay 141 in the form of a circle to identify the controls that the user must manipulate, any other indicia may be used for the contextual overlay such as a blinking or color coded outline, arrow, etc. In one embodiment, the graphic processing module 110 may be configured to receive input from the user concerning the specific configuration of the overlay for identifying a control to be manipulated. If the user is not looking at the correct panel or screen, there can also be visual cues to get the user to change their head position and/or gaze to view the correct panel or screen.

The user may perform the image acquisition process utilizing the interactive display device 134 and module 132 and the contextual overlays 116 generated on the augmented reality display device 106 simplify the workflow of the procedure and reduce errors by providing clear instructions concerning which steps are to be performed and how they are to be performed. In certain embodiments, the determination module 124 may receive feedback from feedback devices 112 and/or signals from the controls input into the interactive medical device 102 by the user to determine the appropriate steps which need to be performed. The determination module 124 is then configured to send signals to the graphic processing module 110 for generating contextual overlays for the determined steps. This permits the system 100 to provide adaptive guidance to the user through the generated contextual overlays 116.

While the contextual overlays 116 generated by the graphic processing module 110 are discussed with respect to an image acquisition process, the contextual overlays may be generated to guide the user 101 through any other procedures. For example, in one embodiment, overlays may be generated by the graphic processing module 110 which guide the user to manipulate a geometry module in order to move the c-arm of an imaging device to a specific position or orientation. However, the overlays 116 generated by the graphic processing module 110 may be utilized for many other interventional procedures and with respect to numerous different types of interactive devices. The contextual overlays 116 identify and provide clearer, more comprehensive and more customizable information which identifies the steps of the procedure to be performed as compared to existing devices, such as flashing LED lights that are located near a particular button which are triggered to indicate that the button should be pressed.

Furthermore, the overlays 116 generated by the graphic processing module 110 may be utilized to provide instructions for new technologies, protocols or devices associated with the interactive medical device 102. For example, the database 122 may be configured to receive updated information concerning new technologies, protocols or devices that are incorporated in the interactive medical device 102 or may be performed by the interactive medical device. The contextual overlays 116 are then generated by the graphic processing module 110 to guide the user through the use of the device or in the performance of the new protocol.

Figure 4:
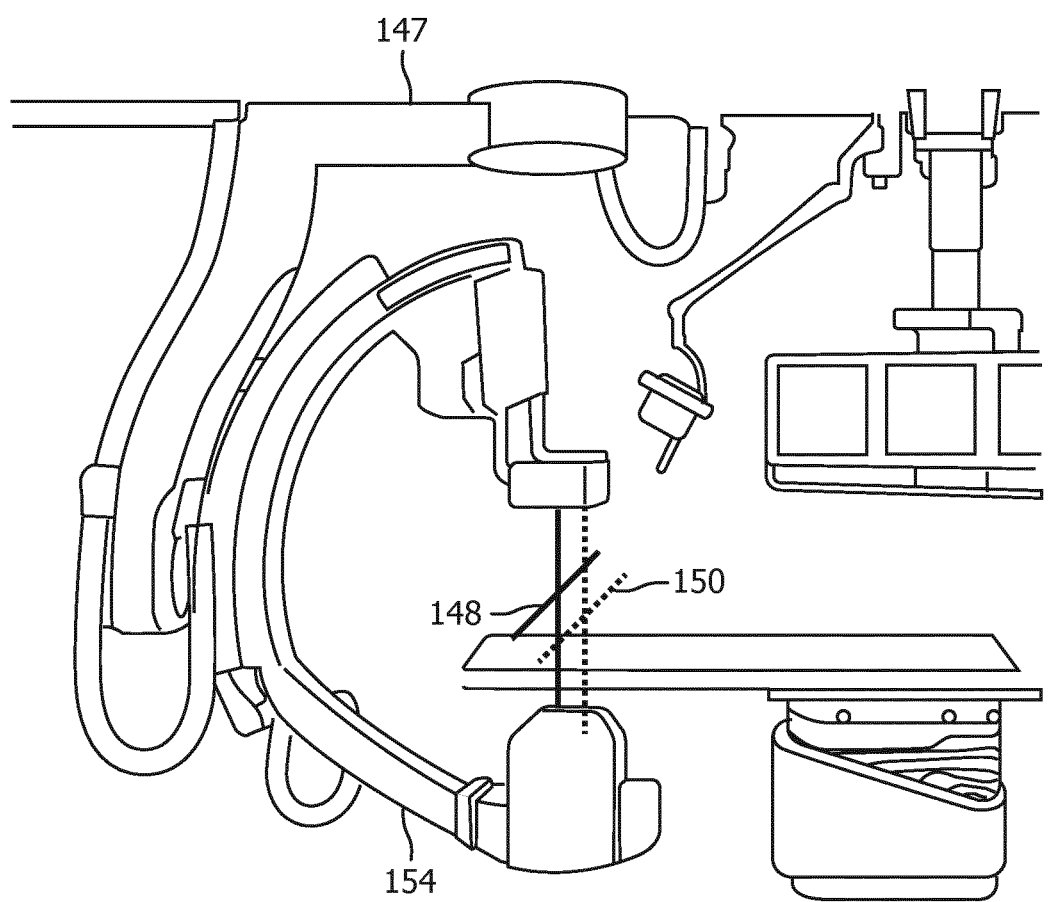
FIG. 4 shows images of contextual overlays for a current and target isocenter displayed on an augmented reality display device in relation to an imaging device having a c-arm.

In another embodiment, the graphic processing module 110 is configured to generate a contextual overlay that identifies a specific region(s) in the environment. For example, FIG. 4 shows an image 147 of an imaging device having a c-arm 154 on an augmented reality display device 106. As shown in FIG. 4, in order to assist the user in isocentering the c-arm, the graphic processing module 110 may be configured to provide contextual overlays 116 which identify the current center of a c-arm and the target isocenter of the c-arm. In FIG. 4, the graphic processing module 110 is configured to generate a crosshair 148 on the augmented reality display device 106 identifying a current isocenter of the c-arm. The graphic processing module 110 is also configured to generate a crosshair 150 identifying the target isocenter.

In one embodiment, the system 100 includes a positional module 152 which is configured to determine the current and target isocenters and send this information to the graphic processing module 110 for generating the contextual overlays, such as the crosshairs 148, 150. The user 101 may then view the position of the c-arm 154 and the current and target crosshair isocenters 148, 150 and adjust the table until the crosshairs line up and the current isocenter is positioned on the overlay identifying the target isocenter. The contextual overlays 116 generated by the graphic processing module 110 increase the ease and accuracy of the isocentering step. The contextual overlays 116 reduce incorrect isocentering which requires additional imaging on the subject 111 and results in increased radiation exposure to the subject. The crosshairs may alternatively be a sphere or other object to represent the isocenter. The crosshairs may also be overlaid onto the fluoroscopy image displayed on the Live imaging or Review screens.

Figure 5:
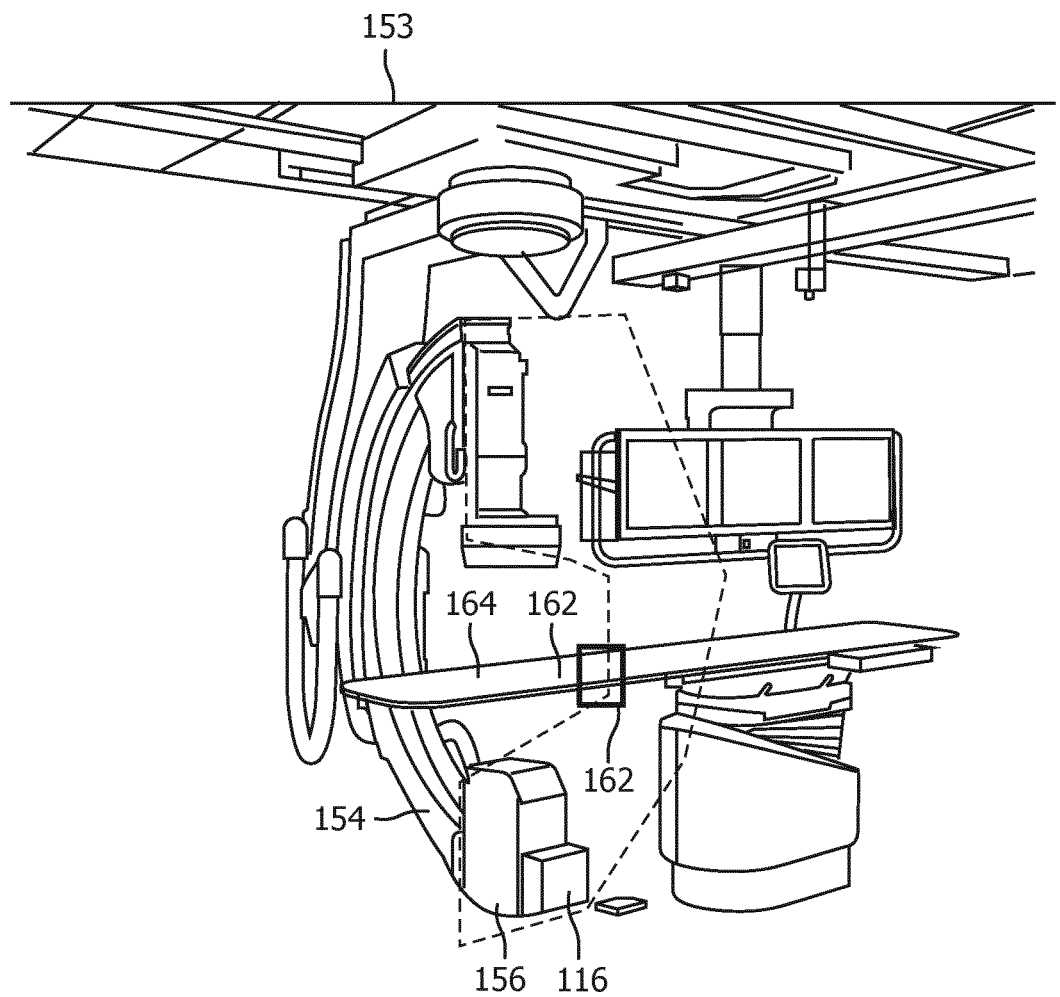
FIG. 5 shows images of contextual overlays which identify a region that must be clear of obstructions on an augmented reality display device in relation to an imaging device having a c-arm.

In another embodiment, the graphic processing module 110 is configured to generate a contextual overlay 116 that identifies regions in the environment that must be clear of obstructions for performing a procedure. For example, FIG. 5 shows an image 153 of an imaging device having a c-arm 154 on an augmented reality display device 106. The graphic processing module 110 is configured to generate a contextual overlay 156 which represents the areas needed for clearing during an image acquisition process so that the c-arm 154 may freely move without hitting any objects. The user when viewing the contextual overlay 156 on the augmented reality display device can easily determine if an object is within the region that requires clearance and may then remove the object from the region.

In one embodiment, the system 100 includes a location module 160 that is configured to inspect or monitor the region that requires clearance and determine if there is an object within that region. The location module 160 is configured to send a signal to the graphic processing module 110 concerning any object that is determined to be within the region that requires clearance. The graphic processing module 110 may be configured to generate a contextual overlay 116 on that object in the augmented reality display device 106 indicating that the object must be removed. For example, in FIG. 5, a contextual overlay comprising a rectangular shaped object 162 is positioned over a portion of the table 164 indicating that the table must be repositioned to be out of the region which requires clearance.

The contextual overlays 116 generated by the graphic processing module 110 avoid encumbrances in the c-arm region while the interventional procedure is performed. These encumbrances typically require the user to spend significant time in order to move the objects so that the c-arm may rotate freely. It is important to overlay the region representing the current c-arm position correctly. The current c-arm position may be computed automatically through camera-based detection, a tracking marker, a tracking technology, the c-arm encoding, or manually by the user.

While the contextual overlays 116 are illustratively shown as identifying objects within a region that requires clearance or for identifying isocenters, the contextual overlays may be configured to identify any other objects or regions in the environment 108 and with respect to any interventional procedure.

In other embodiments, the location module 160 may determine objects within a path of a movable device and determine an updated path for the movable device. The graphic processing module 110 is configured to generate a contextual overlay 116 identifying the new path and/or guiding the user to move the movable device along the path.

In another embodiment, the system 100 enhances the user's performance of the procedure by configuring the graphic processing module 110 to generate contextual overlays 116 that reduce the subject 111 to exposure from radiation. For example, in one embodiment, the contextual overlays 116 include prompts for the user to check the fluoro flavor. The graphic processing module 110 may be configured to receive instructions from the database 122 or from user input to determine a preferable time period for prompting the user to check the fluoro flavor.

In other embodiments, the system 100 may include a real-time dose monitoring device and the graphic processing module 110 may be configured to generate contextual overlays 116 identifying individuals that have received a high dose of radiation based on measurements from the real-time dose monitoring device. The system 100 may also generate contextual overlays 116 which recommend when to use wedges, move a radiation detector, etc. based on instructions from the database 122, from user input or in response to radiation detected by the dose monitoring device.

In other embodiments, the graphic processing module 110 may be configured to generate contextual overlays 116 which provide optimal locations for various objects in the environment 108. For example, in one embodiment, contextual overlays 116 may provide the desired set-up of the interactive medical device 102, components 104 and subject 111 prior to the performance of the interventional procedure so that the environment 108, such as an operating room, may be set up in an optimal state prior to the practitioner's arrival. The optimal orientation of the room may be included in instructions in the database 122 or may be input by the user prior to the interventional procedure.

Figure 6:
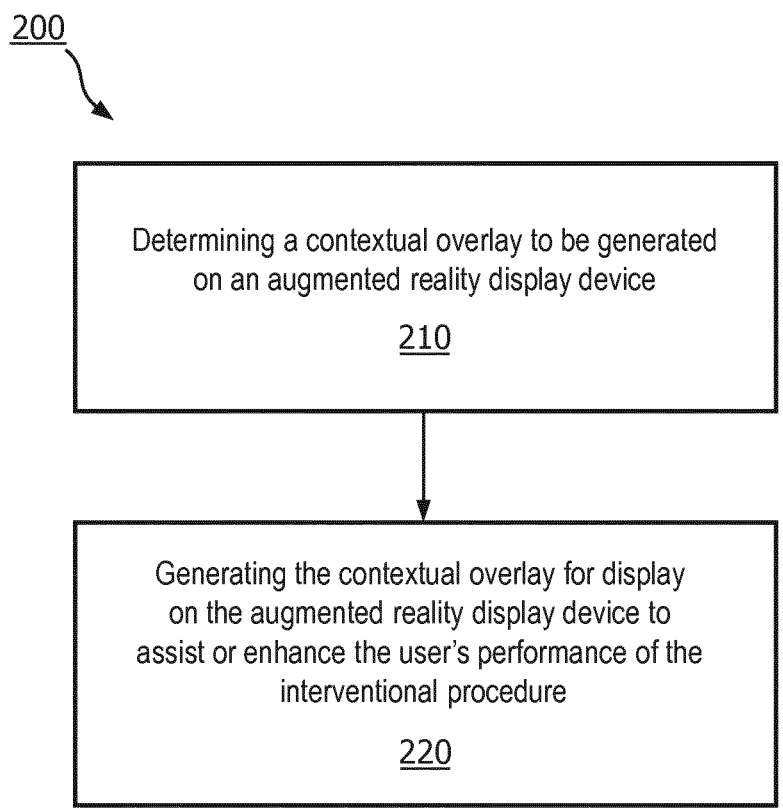
FIG. 6 is a flow diagram showing a method for assisting or enhancing a user's performance of an interventional procedure in accordance with one embodiment.

Referring to FIG. 6, methods 200 for assisting or enhancing a user's performance of an interventional procedure in an environment using an interactive medical device, are illustratively shown in accordance with the present principles. In block 210, a contextual overlay to be generated on the augmented reality display device is determined. In block 220, the contextual overlay is generated on the augmented reality display device to assist or enhance the user's performance of the interventional procedure.

As previously described with respect to embodiments of the system 100, the method may include the step of receiving input from the user concerning the contextual overlay in order to generate a customized contextual overlay. Alternatively, feedback from the user, a subject and/or the interactive medical device during the interventional procedure may be used to determine the contextual overlay that is generated on the augmented reality display device.

As previously described, methods may include generating contextual overlays that identify at least one component of the interactive medical device. The contextual overlays may also identify at least one step of the interventional procedure to be performed by the user. The contextual overlays may also identify a specific region in the environment, such as a target or current isocenter, a region that is required to be clear of encumbrances, a desired position of a c-arm, etc.

In one embodiment, feedback from at least one of: a feedback device that is configured to receive feedback from the user, a subject and/or the interactive medical device during the interventional procedure, a history of signals from one or more of the plurality of components or a database is used to determine the at least one step of the interventional procedure to be performed by the user. The method may also adaptively provide contextual overlays to the user for identifying an optimal path of a device, reducing radiation, etc.

In interpreting the appended claims, it should be understood that:

a) the word "comprising" does not exclude the presence of other elements or acts than those listed in a given claim;

b) the word "a" or "an" preceding an element does not exclude the presence of a plurality of such elements;

c) any reference signs in the claims do not limit their scope;

d) several "means" may be represented by the same item or hardware or software implemented structure or function; and e) no specific sequence of acts is intended to be required unless specifically indicated.

Having described preferred embodiments for an augmented reality interventional system providing contextual overlays and methods therefor (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A medical interventional system, comprising:
   an interactive medical device including a plurality of components;
   an augmented reality display device worn by a user and configured to show an image of at least one component of the plurality of components of the interactive medical device viewed by the user during an interventional procedure in an environment using the interactive medical device; and
   a processor connected to memory and configured to generate a contextual overlay over the image of the at least one component shown on the augmented reality display device, wherein the processor is configured to generate the contextual overlay to include identification of control of the at least one component to assist the user in performing the interventional procedure using the interactive medical device.

2. The system as recited in claim 1, wherein the processor is further configured to:
   receive feedback from at least one of the user, a subject, and the interactive medical device during the interventional procedure; and
   receive the feedback and provide the contextual overlay based on the feedback.

3. The system as recited in claim 1, wherein the processor is further configured to receive input from the user to determine the contextual overlay that is generated.

4. The system as recited in claim 1, wherein the processor is further configured to generate the contextual overlay to include an identification of a step of the interventional procedure to be performed by the user.

5. The system as recited in claim 4, wherein the processor is further configured to identify the step of the interventional procedure including identifying one or more specific controls to be manipulated by the user and describing a manipulation of the one or more specific controls.

6. The system as recited in claim 4, wherein the processor is further configured to:
   receive feedback from at least one of the user, a subject, and the interactive medical device during the interventional procedure; a history of signals from the at least one component of the plurality of components of the interactive medical device; or a database;
   determine the step for the user to perform for the interventional procedure based on the feedback; and
   send signals concerning the contextual overlay to be generated for the step.

7. The system as recited in claim 1, wherein the processor is further configured to generate the contextual overlay to include identification of a specific region in the environment.

8. The system as recited in claim 7, wherein the processor is further configured to generate the contextual overlay to include identification of a desired position for a c-arm of the interactive medical device.

9. The system as recited in claim 1, wherein the processor is further configured to:
   determine a position of a target isocenter for a c-arm of the interactive medical device and a current isocenter for the c-arm; and
   based on the position of the target isocenter and a current isocenter, generate the contextual overlay to include identification of the target isocenter and another contextual overlay to include identification of the current isocenter in the environment.

10. The system as recited in claim 1, wherein the processor is further configured to generate the contextual overlay to include identification of at least one region that must be clear of obstructions for performing the interventional procedure.

11. The system as recited in claim 10, further comprising:
    determine positions of objects in the environment and compare the positions of objects with the at least one region that must be clear of obstructions; and
    generate the contextual overlay to include identification of objects in the at least one region that must be clear of obstructions.

12. A method for assisting performance of an interventional procedure by a user in an environment, the method comprising:
    providing an interactive medical device including a plurality of components;
    displaying, by an augmented reality display device worn by the user, an image of at least one component of the plurality of components of the interactive medical device viewed by the user while performing the interventional procedure; and
    generating a contextual overlay over the image of the at least one component displayed by the augmented reality display device, the contextual overlay identifying the at least one component to assist the user's performance of the interventional procedure.

13. The method as recited in claim 12, further comprising determining the contextual overlay based on feedback from at least one of the user, a subject, and the interactive medical device acquired during the interventional procedure.

14. The method as recited in claim 12, wherein the contextual overlay is configured to identify at least one step of the interventional procedure to be performed by the user by identifying one or more specific controls to be manipulated by the user and describing a manipulation of the one or more specific controls.

* * * * *